United States Patent [19]

Chu et al.

[11] Patent Number: 5,073,246

[45] Date of Patent: Dec. 17, 1991

[54] SLAB ELECTROPHORESIS SYSTEM WITH IMPROVED SAMPLE WELLS AND COOLING MECHANISM

[75] Inventors: Daniel Y. Chu, Hercules; John J. Barich, Martinez, both of Calif.

[73] Assignee: Bio-Rad Laboratories, Inc., Hercules, Calif.

[21] Appl. No.: 523,786

[22] Filed: May 16, 1990

[51] Int. Cl.[5] .................... G01N 27/26; B01D 57/02
[52] U.S. Cl. .............................. 204/299 R; 204/182.8
[58] Field of Search ....................... 204/299 R, 182.8

[56] References Cited

U.S. PATENT DOCUMENTS

| | | | |
|---|---|---|---|
| 3,208,929 | 9/1965 | Raymond et al. | 204/299 R |
| 3,402,118 | 9/1968 | Mutter | 204/299 |
| 3,579,433 | 5/1971 | Dahlgren | 204/299 |
| 3,677,930 | 7/1972 | Meshbane et al. | 204/299 R |
| 3,856,655 | 12/1974 | Roberts | 204/299 |
| 3,879,280 | 4/1975 | Peterson et al. | 204/299 |
| 3,888,759 | 6/1975 | Elson et al. | 204/299 |
| 3,932,265 | 1/1976 | Hoefer | 204/299 |
| 3,980,540 | 9/1976 | Hoefer | 204/180 |
| 4,325,796 | 4/1982 | Hoefer et al. | 204/180 |
| 4,339,327 | 7/1982 | Tyler | 204/299 R |
| 4,431,506 | 2/1984 | Gorman, Jr. et al. | 204/299 R |
| 4,574,040 | 3/1986 | Delony et al. | 204/182.8 X |
| 4,612,106 | 9/1986 | Kromer et al. | 204/299 R |
| 4,624,768 | 11/1986 | Yoshida et al. | 204/182.8 X |
| 4,668,362 | 5/1987 | November et al. | 204/182.8 |
| 4,795,541 | 1/1989 | Hurd et al. | 204/299 R |
| 4,883,577 | 11/1989 | Sugimoto et al. | 204/182.8 X |
| 4,909,918 | 3/1990 | Bambeck et al. | 204/182.8 X |
| 4,975,174 | 12/1990 | Bambeck et al. | 204/182.8 X |

FOREIGN PATENT DOCUMENTS

| | | | |
|---|---|---|---|
| 2377626 | 8/1978 | France . | |
| 5749852 | 3/1982 | Japan . | |
| 613044 | 1/1986 | Japan | 204/299 R |
| 59-123607 | 2/1986 | Japan | 204/182.8 |
| 6480850 | 3/1989 | Japan | 204/299 R |
| 8600708 | 1/1986 | PCT Int'l Appl. . | |

Primary Examiner—John Niebling
Assistant Examiner—John S. Starsiak, Jr.
Attorney, Agent, or Firm—Townsend & Townsend

[57] ABSTRACT

A gel enclosure and buffer tank for vertical slab gel electrophoresis are disclosed. The gel enclosure is formed from two flat plates, one of which contains angled troughs extending off to one side to serve as extensions of the sample wells, thereby increasing the volumetric capacity of each sample well, and improving the ease of loading it with sample. The buffer tank is constructed in such a manner as to hold one flat plate of the gel enclosure in contact with a flat heat transfer wall of the buffer tank, with cooling applied to the outside of the wall by thermoelectric means. Buffer solution below the gel enclosure is also cooled by the cooling wall, and bubbles generated at an electrode, also positioned below the gel enclosure, agitate the cooled buffer solution, extending the cooling effect over the entire surface of the other flat plate of the gel enclosure.

19 Claims, 3 Drawing Sheets

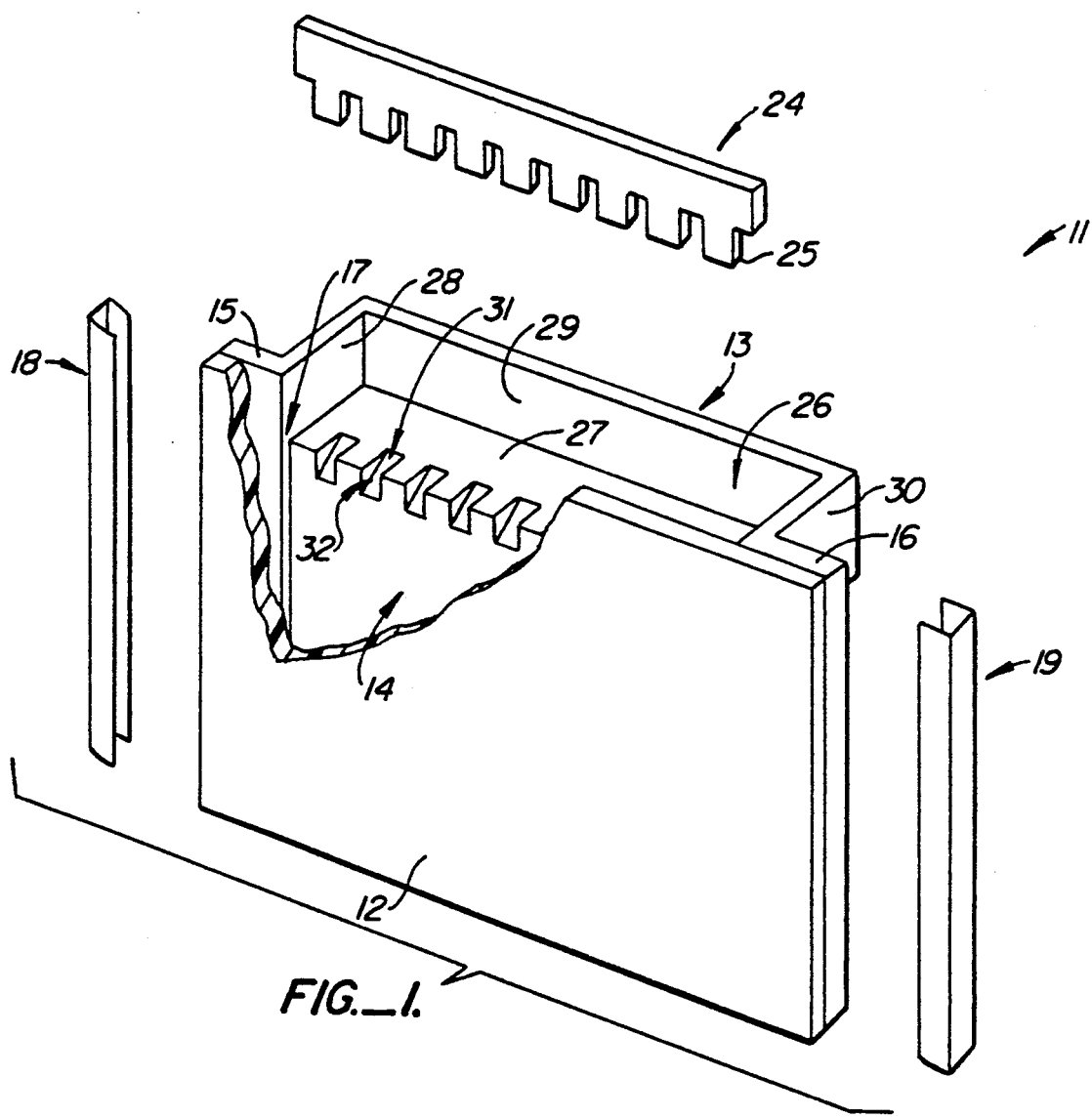
FIG._1.
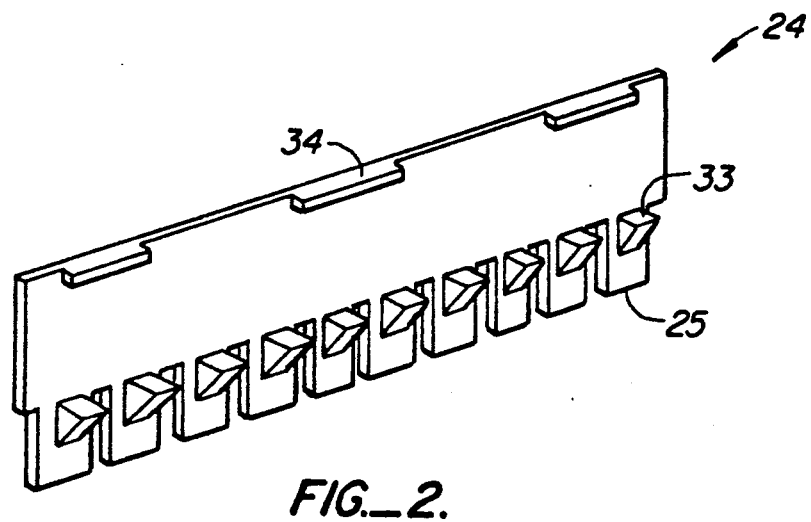
FIG._2.

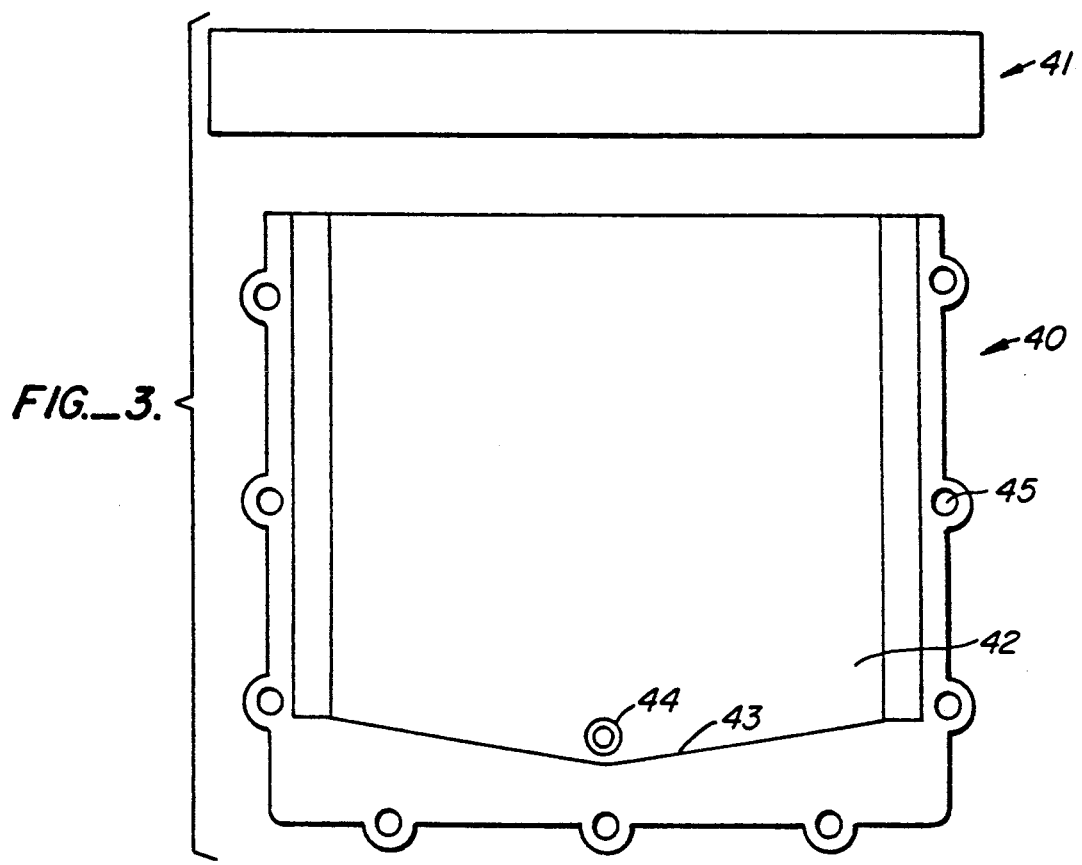
FIG._3.
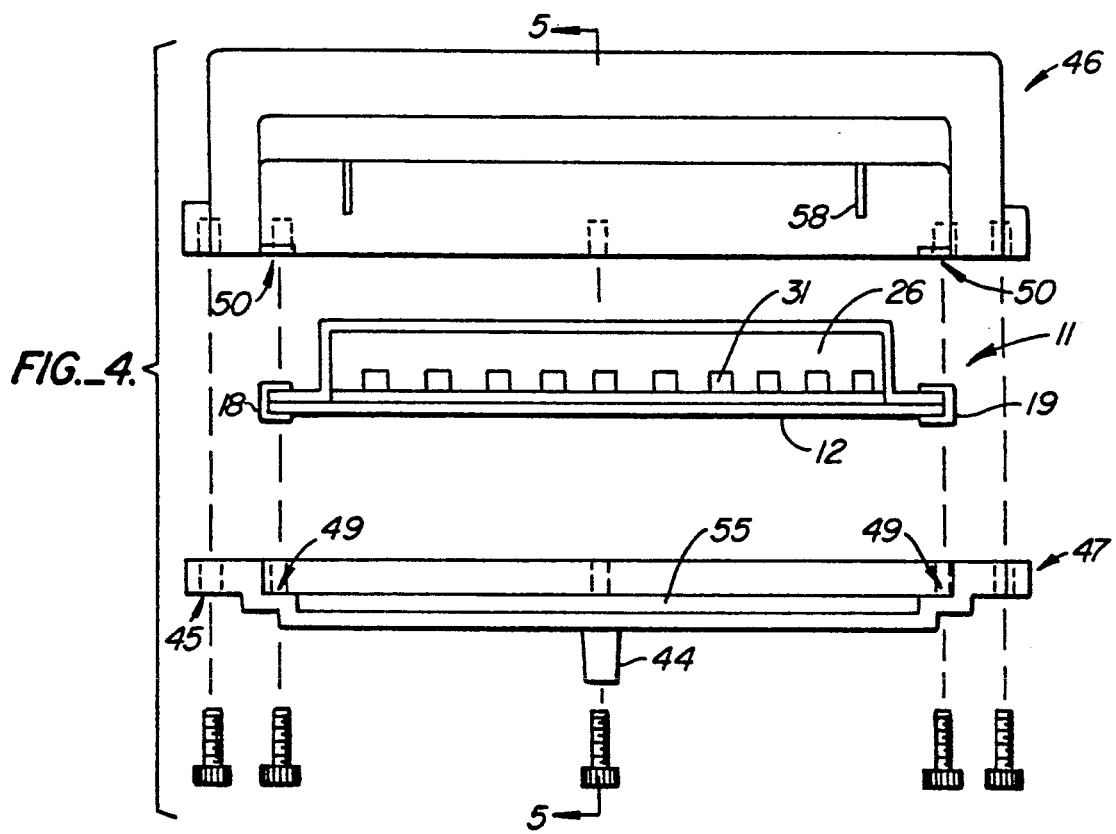
FIG._4.

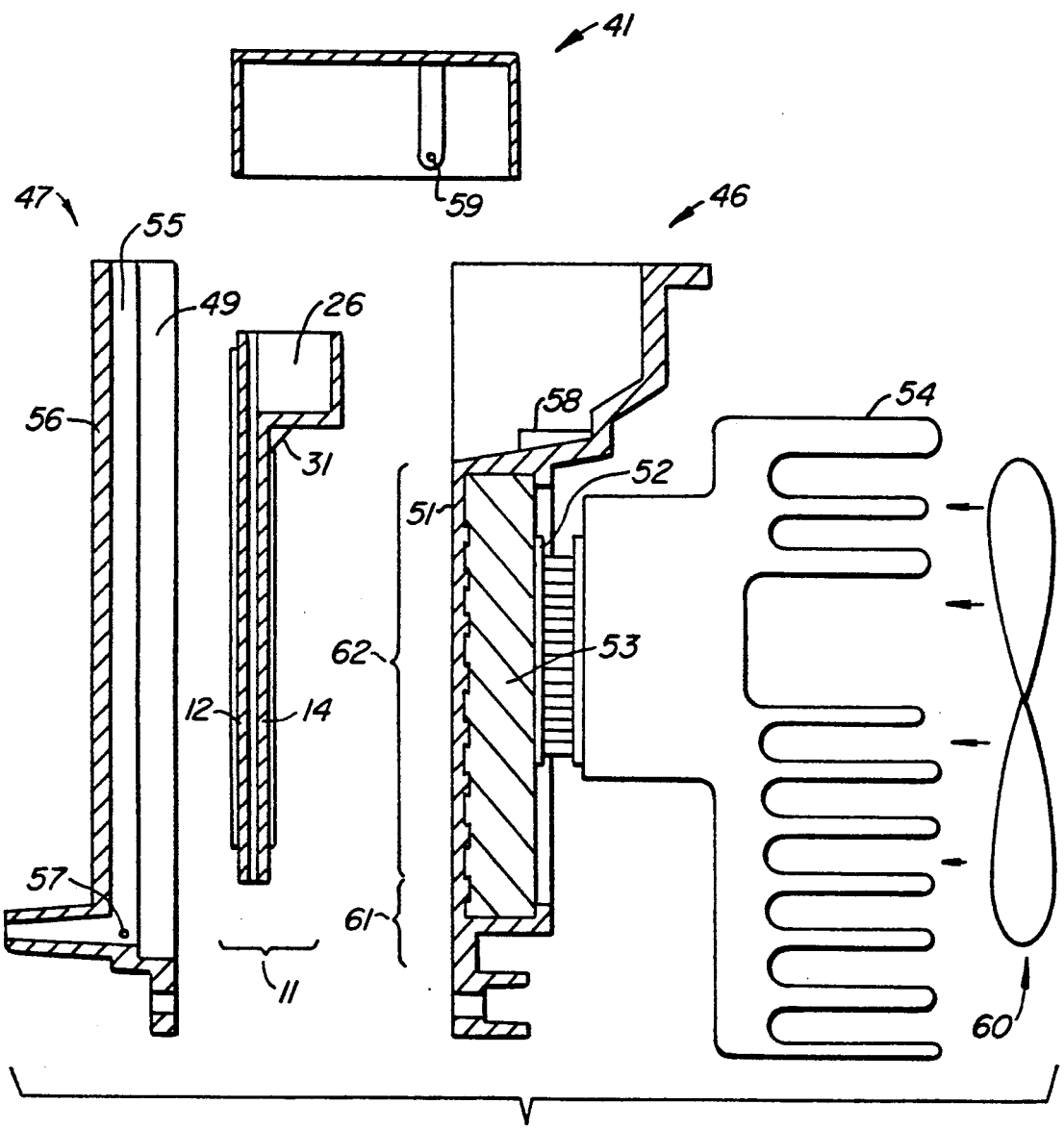
FIG._5.

SLAB ELECTROPHORESIS SYSTEM WITH IMPROVED SAMPLE WELLS AND COOLING MECHANISM

This invention lies in the field of vertical slab gel electrophoresis. In particular, this invention addresses problems associated with loading samples onto a slab gel and cooling the gel during electrophoresis.

BACKGROUND OF THE INVENTION

Some of the many considerations in designing apparatus for vertical slab gel electrophoresis are cooling to maintain uniform and constant temperature, the maintenance of a steady and uniform electric field, minimizing the volumes of buffer solutions needed, and loading samples in a reliable and reproducible manner.

Gel slabs are usually formed by joining two glass plates together with spacers at both vertical edges to establish a gap between them usually measuring 0.25-3 mm in width. The plates are clamped together along the vertical edges and a seal is placed along the open bottom edge. The gap is then filled with gel solution and a well-forming insert, referred to in the industry as a "comb" or a "template," is placed along the open upper edge with teeth extending into the space between the plates. The gel is allowed to set with this insert in place, and the insert is then removed to leave a row of wells along the top edge of the gel. Samples are placed in these wells after the seal along the bottom edge of the gel is removed and the resulting "gel sandwich" is placed in a cell. Then, the upper and lower exposed edges are placed in contact with conductive buffers in which electrodes are also immersed.

Thin gels are desirable for many separations. Unfortunately, thin gels have thin sample wells, which limit the volume of sample which can be loaded, and also make it difficult to place the sample in the well.

Another problem addressed herein is one which arises with all types of electrophoresis-joule heating. As in other electrophoretic systems, slab gel systems are susceptible to this heating effect, particularly when a high-strength electric field is used. As is well known among those skilled in the art, uncontrolled joule heating can cause damage to the samples, and nonuniform temperatures will cause proteins at different locations of the gel to migrate at different speeds.

SUMMARY OF THE INVENTION

The apparatus disclosed herein contains features addressing both of these problems. In one aspect of the invention, one plate of the two-plate arrangement which forms the gel enclosure contains a series of angled troughs along the sample loading edge, each trough opening into the space between the plates. The spacing of the troughs corresponds to the spacing of the teeth in the comb-shaped insert used to form the sample wells in the gel, and the troughs serve to widen the sample wells to increase their capacity. In preferred embodiments, the teeth of the comb-shaped insert are both longer and wider than the troughs so that the teeth cover the trough openings, and in still further preferred embodiments, a projection extends from each of the teeth such that the projections will extend into the troughs when the insert is in place. These projections may serve to support the insert at an appropriate height, or fill the interior space of each trough, to leave open space in the trough free of gel while the gel is being cast, or both. Once the gel is cast and the insert is removed, the troughs will both increase the sample size which the system can accommodate, and make it considerably easier for the operator to place samples in the wells without risking damage to the gel itself.

In a second aspect of the invention, the slab gel enclosure is arranged in a buffer tank in a manner which places an electrode in electric contract with the lower exposed edge of the gel, through the buffer solution. The tank is constructed such that one flat wall is cooled from the outside by a thermoelectric cooling device while the inside surface of the wall is in contact with one plate of the gel enclosure. The lower edge of the gel enclosure is raised above the floor of the tank, leaving a section of the cooled wall below the gel enclosure. Opposite this exposed portion of the cooled wall is the electrode, positioned such that gas bubbles generated at the electrode draw cooled buffer solution from underneath the gel enclosure up along its opposite wall, thereby extending the cooling effect to both sides of the gel enclosure in a uniform manner. Some of these features are described below as preferred embodiments of this aspect of the invention, and further preferred embodiments include such features as a slab of heat-dispersing material secured to the outside of the cooled wall of the buffer tank, positioned between the wall and the cooling device, as well as the use of dissimilar materials for the two flat walls of the gel enclosure, and selection of the surface areas of the tank wall and gel enclosure wall to account for the difference in thermal conductivity between the two materials.

These two aspects of the invention may be embodied individually in separate structures, or may be combined in a single structure. Further features, advantages and embodiments of each of these two aspects will be apparent from the description which follows.

BRIEF DESCRIPTION OF THE DRAWINGS

FIG. 1 is a perspective, partially expanded view of a gel enclosure in accordance with the invention, including a comb-shaped insert for forming sample wells in the gel.

FIG. 2 is a perspective view of the comb-shaped insert of FIG. 1, showing the opposite side.

FIG. 3 is a front elevation of a buffer tank in accordance with the invention, designed to receive and retain the gel enclosure of FIG. 1.

FIG. 4 is a top view, expanded, of the buffer tank of FIG. 3, including the gel enclosure of FIG. 1.

FIG. 5 is a side cutaway view of the buffer tank and gel enclosure of FIG. 4, taken along the line 5—5 thereof.

DETAILED DESCRIPTION OF THE INVENTION AND PREFERRED EMBODIMENTS

The gel enclosure 11 shown in FIG. 1 is offered as an illustrative example of the first aspect of the invention. The enclosure is formed of first and second members 12, 13 which enclose the gel along its two flat faces and its two lateral edges, leaving the top and bottom edges exposed. The first member 12 in this illustration is a flat plate, whereas the second member 13 is a molded structure, one portion of which is a flat plate 14 facing the other flat plate 12. The materials from which these members are constructed should be non-conductors of electricity, but otherwise are not critical, the primary considerations being transparency to permit visual monitoring of the gel formation and the electrophoretic process, and heat transfer characteristics to permit cooling through the walls of these members. For ease of manufacture, the first member 12 is preferably a glass plate for stiffness, while the second member 13 is preferably clear plastic, such as acrylic.

The second member 13 in this illustration contains flat strips 15, 16 on either side of the flat portion 14. These strips serve as the contact areas between the two members. The two strips serve a further purpose by defining a plane which is forward of the plane of the flat plate portion 14, thereby providing narrow shoulders 17 equal in width to the thickness of the gel. The plate spacing may also be formed by other conventional means, such as placing spacers of appropriate thickness between the two members. The structure shown in the drawing incorporates spacers into the second member 13, and offers the advantage of facilitating the alignment of the parts, and requiring fewer component parts of the entire assembly. The gap defines space which serves as both the mold cavity for the gel and the space to be occupied by the gel during electrophoresis. The space is bordered by the flat plate (the first member 12 of the gel enclosure), the flat plate portion 14 of the second member 13 of the gel enclosure, and the two narrow shoulders 17 along the flat strips on either side.

The two members 12, 13 are held together by conventional means, which generally include any of various types of clamps or clips along the lateral edges. The clips shown in FIG. 1 are U-shaped plastic clips 18, 19 which slide over the contacting lateral edges, and have sufficient strength and resiliency to keep the two members together during electrophoresis. Additional clamping forces can be applied on these clips during the casting of the gel.

The comb-shaped insert 24 fits in the gap between the first flat plate 12 and the flat plate section 14 of the second member 13. The teeth 25 of the insert extend downward to form wells in the gel. As the other figures hereto will demonstrate, the insert 24 is designed to rest along the top edge of the gel space, with only the teeth 25 extending into the gel space.

The construction of the second member 13 of the gel enclosure includes a walled extension 26 along the top of the flat plate section 14. This extension 26 forms an upper buffer chamber to provide electrified buffer contact with the upper edge of the gel. The extension includes a floor 27 and three walls 28, 29, 30. The flat plate 12 which forms the other member of the gel enclosure serves as the fourth wall.

The edge of the floor 27 which runs adjacent to the gel space contains a series of troughs 31 arranged at the locations where the wells will be formed by the teeth 25 of the comb-shaped insert 24. Each trough intersects the upper edge of the flat plate portion, and forms an opening 32 along the flat plate portion 14. These openings 32 will open into each of the various sample wells formed in the gel by the teeth 25 of the insert. The troughs are angled, forming an obtuse angle with the flat plate portion 14. In preferred embodiments, this angle will be about 110° to about 160°. Once the gel is cast and the insert 24 removed, samples may be added in sufficient volume to fill not only the wells formed in the gel but also the interior of each trough, the troughs thereby considerably increasing the volumetric capacity of each well.

FIG. 2 offers a view of the opposite side of the comb-shaped insert 24. Each of the teeth 25 has a projection 33. These projections extend into the troughs 31 when the insert is in place. The projections have angled lower surfaces, like the troughs, and generally complement the troughs in shape, leaving a void in each trough after the gel is cast and the insert removed. Each void thus forms part of the well volume. It will be noted that each tooth 25 is both wider and longer than each projection 33, in the same manner that the teeth are wider and deeper than the troughs.

Also included on the insert are finger grips 34, facilitating removal of the insert by the operator after the gel has been cast.

FIG. 3 is a front view of a buffer tank 40, designed as a receptacle for the lower buffer solution and a housing for the lower electrode, as well as to receive the entire gel enclosure. A lid 41 is shown above the buffer tank, the lid containing an electrode which will serve as the upper electrode when the lid is in place. The cavity 42 of the buffer tank has a V-shaped floor 43 and a drainage port 44 toward the vertex of the V, facilitating the removal of buffer solution from the tank. As shown in the subsequent figures, the buffer tank 40 in this embodiment is constructed in two halves, sealed together in liquid-tight manner along the bottom and two sides by bolts and nuts or other conventional means. Nine bolt passages 45 are shown in FIG. 3.

Turning next to FIG. 4, the buffer tank is shown from above in an expanded view, together with the gel enclosure 11. In this view, the two halves 46, 47 of the buffer tank are visible, as are the bolts 48 which hold the two halves together. A vertical cutaway view is shown in FIG. 5.

Viewing FIGS. 4 and 5 together, the interior of the forward half 47 of the buffer tank is seen to have a stepped profile 49 on both sides. The rear half 46 of the buffer tank contains corresponding indentations 50. When the two halves are secured together, the stepped profile and indentations together form a groove along each edge of the tank cavity, each groove sized to receive one of the two lateral edges of the gel enclosure 11, and large enough to accommodate the end clips 18, 19. The grooves are positioned in such a manner that they hold the gel enclosure 11 in the desired position in the tank, with the outer surface of the flat wall portion 14 of the molded plate of the gel enclosure in contact with a flat wall 51 in the rear half 46 of the buffer tank. This flat wall 51 is cooled by a thermoelectric cooling device 52, through a slab of highly heat conductive material 53 which spreads the cooling effect over the entire surface of the flat wall 51. The thermoelectric cooling device 52 may be any of a variety of commercially available units. One example is such a device, which is particularly useful for a plastic wall 51 of a thickness of 0.025 inch and constant power electrophoresis at 15 W, is the use of two cooling elements supplied by Melcor Materials Electronic Products Corporation, Trenton, N.J., U.S.A., identified as Thermoelectric Heat Pump Modules, catalog no. CP 1.4-127-045L. The elements are connected in series to a 15 VDC source.

The heat conductive material 53 will generally be a material having a thermal conductivity of at least about 120 W/mK at 20° C., preferably at least about 229 W/mK at 20° C. The material may, for example, be a metallic slab such as copper or aluminum (grade 2024 or 1100). A finned heat sink 54 and a fan 60 are also shown, to complete the cooling apparatus. The arrows to the left of the fan indicated the direction of the air flow created by the fan.

The stepped profile 49 of the forward half 47 of the buffer tank also leaves a gap 55 between the forward flat plate 12 of the gel enclosure and the forward wall 56 of the buffer tank. In operation, this gap will be occupied by lower buffer solution, extending the height of the gel in the gel enclosure 11. An electrode 57 is positioned near the bottom of this gap and near the surface of plate 12, serving as the anode. Bubbles generated by the anode during electrophoresis will rise vertically up the gap, agitating the buffer solution. While the width of this gap 55 is not critical, it should be wide enough to permit the bubbles to agitate the buffer solution. A gap of uniform width of not less than about 0.1 cm is preferred. An actual gap of 0.3 to 0.6 cm has been used succesfully.

The height of the gel enclosure 11 in the buffer tank is established by a pair of support ribs 58, on which the underside of the upper buffer chamber 26 will rest. These ribs 58 are of such a height that the gel enclosure 11 will not extend down the full length of the cooled surface 51, but instead leave a strip 61 along the bottom of the cooled surface beneath the lower edge of the gel enclosure 11, exposed to the lower buffer solution. The lower buffer solution contacting this strip 61 will be directly cooled by it, and the bubbles generated at the electrode 57 will mix this cooled liquid with the remaining liquid occupying the gap 55 above it, extending the cooling effect to the entire front plate 12 of the gel enclosure. For maximum effect, the ratio of the portion 62 of the surface area of the cooled wall 51 which contacts the rear plate 14 of the gel enclosure to the surface area of the exposed strip 61 will be approximately equal to the ratio of the thermal conductivity of the forward plate 12 of the gel enclosure to that of the rear plate 14. Since the rear flat plate 14 will generally be of a lower thermal conductivity than the forward flat plate 12, the surface area of the contacting portion 62 of the cooled wall 51 will generally be greater than the surface area of its exposed strip 61.

It will also be noted that the lid 41 contains an upper electrode 59 as a cathode, positioned in such a manner that the upper electrode will extend into the upper buffer chamber of the gel enclosure, which will be filled with an upper buffer solution during electrophoresis.

The foregoing is offered primarily for purposes of illustration. It will be readily apparent to those skilled in the art that numerous variations and substitutions may be made in the materials, shapes, configurations, and structures disclosed herein without departing from the spirit and scope of the invention.

What is claimed is:

1. Apparatus for vertical slab gel electrophoresis, comprising:
   a slab gel enclosure having opposing first and second flat walls defining a rectangular slab gel space in between which is open along one edge, said open edge defining the width of said rectangular slab gel space;
   a buffer tank sized to contain said slab gel enclosure, said buffer tank including opposing third and fourth flat walls and a floor in between, said third flat wall at least coextensive with said rectangular slab gel space in width and height;
   securing means for securing said slab gel enclosure inside said buffer tank with said first and third flat walls in contact and with a first gap between said open edge of said slab gel enclosure and said floor and a second gap between said second and fourth walls;
   an electrode in said buffer tank positioned such that when said slab gel enclosure is so secured therein, said electrode is in said first gap; and
   cooling means for drawing heat from said third flat wall.

2. Apparatus in accordance with claim 1 further comprising heat dispersing means for equalizing temperatures over the length and width of said third wall.

3. Apparatus in accordance with claim 1 in which said third flat wall exceeds said rectangular gel space in height, and said securing means provides a strip of said third flat wall along said floor adjacent to said first gap.

4. Apparatus in accordance with claim 3 further comprising heat dispersing means for equalizing temperatures over the length and width of said third wall including said strip.

5. Apparatus in accordance with claim 4 in which said heat dispersing means is comprised of a slab of solid material contacting and substantially coextensive with said third flat wall and having a thermal conductivity of at least about 120 W/mK at 20° C.

6. Apparatus in accordance with claim 4 in which said heat dispersing means is comprised of a slab of solid material contacting and substantially coextensive with said third flat wall and having a thermal conductivity of at least about 229 W/mK at 20° C.

7. Apparatus in accordance with claim 1 in which said buffer tank further includes a pair of opposing side walls joining said third and fourth walls, and said securing means comprises grooves in said side walls to receive opposing lateral edges of said slab gel enclosure.

8. Apparatus in accordance with claim 1 in which said slab gel enclosure includes an upper buffer chamber along an upper edge opposite said open edge, and means for supporting an electrode in said upper buffer chamber.

9. Apparatus in accordance with claim 1 in which said second gap is of uniform width of at least about 0.1 cm.

10. Apparatus in accordance with claim 1 in which said first and second flat walls of said slab gel enclosure are of materials differing in thermal conductivity, the material of said first flat wall being of lower thermal conductivity than that of said second flat wall.

11. Apparatus in accordance with claim 10 in which said first and second flat walls are of plastic and glass, respectively.

12. Apparatus in accordance with claim 10 further comprising heat dispersing means for equalizing temperatures over the length and width of said third wall.

13. Apparatus in accordance with claim 1 in which:
   said third flat wall exceeds said rectangular gel space in height such at only a portion of the surface area of said third flat wall is in contact with said first flat wall;
   said securing means provides a strip of said third flat wall along said floor adjacent to said first gap;
   said first and second flat walls of said slab gel enclosure are of materials differing in thermal conductivity, the material of said first flat wall being of lower thermal conductivity than that of said second flat wall; and
   the ratio of the surface area of said portion of said third flat wall contacting said first flat wall to the surface area of said strip of said third flat wall adjacent to said first gap is approximately equal to the ratio of the thermal conductivity of the material of said second flat wall to the thermal conductivity of said first flat wall.

14. Apparatus for casting and retaining a slab gel for use in electrophoresis, said apparatus comprising:
   a first member comprised of a first flat plate of selected width and length;
   a second member comprised of:
      a second flat plate of length less than that of said first flat plate, one edge along the width of said second flat plate defined as an upper edge, and
      a series of troughs extending to one side of said second flat plate at an obtuse angle with respect to said second flat plate, said troughs intersecting said upper edge to define openings in said flat plate along said upper edge;
   means for securing together said first and second members with a portion of said first flat plate extending beyond said upper edge, thereby defining a slab gel space between said first and second flat plates and adjacent to said upper edge; and
   a comb-shaped insert with teeth which are equal in spacing and number, and at least equal in length and width, to said troughs, adapted to rest on said upper edge when said first and second members are so secured together, with said teeth extending into said slab gel space.

15. Apparatus in accordance with claim 14 in which said teeth are greater in length and width than said troughs.

16. Apparatus in accordance with claim 14 in which said second member further comprises a projection along said upper edge extending transverse to said second flat plate, said projection, together with said portion of said first flat plate extending beyond said upper edge when said first and second members are secured together, forming a buffer receptacle along said upper edge, said troughs forming indentations in said projection.

17. Apparatus in accordance with claim 14 in which said comb-shaped insert includes projections on said teeth, said projections substantially complementary in shape to said troughs and positioned on said teeth to reside inside said troughs and substantially fill the interior space thereof when said comb is resting on said upper edge.

18. Apparatus in accordance with claim 14 in which said troughs form an angle of about 110° to about 160° with respect to said second flat plate.

19. Apparatus in accordance with claim 14 in which said second member further comprises a pair of flat surfaces extending the length of said second member along opposing sides of said second flat plate, defining a plane parallel to said second flat plate and displaced therefrom by a selected distance equal to the desired thickness of said slab gel.

* * * * *